(12) United States Patent
Briglin

(10) Patent No.: US 11,569,079 B2
(45) Date of Patent: Jan. 31, 2023

(54) GAS ANALYZER AND MEMBRANES THEREFOR

(71) Applicant: INFICON, Inc., East Syracuse, NY (US)

(72) Inventor: Shawn M. Briglin, Cazenovia, NY (US)

(73) Assignee: INFICON, Inc., East Syracuse, NY (US)

( * ) Notice: Subject to any disclaimer, the term of this patent is extended or adjusted under 35 U.S.C. 154(b) by 0 days.

(21) Appl. No.: 17/229,414

(22) Filed: Apr. 13, 2021

(65) Prior Publication Data

US 2021/0319992 A1 Oct. 14, 2021

Related U.S. Application Data

(60) Provisional application No. 63/008,862, filed on Apr. 13, 2020.

(51) Int. Cl.
| | |
|---|---|
| *H01J 49/24* | (2006.01) |
| *H01J 49/00* | (2006.01) |
| *G01N 33/00* | (2006.01) |
| *G01N 30/72* | (2006.01) |
| *G01N 30/02* | (2006.01) |

(52) U.S. Cl.
CPC ........ *H01J 49/0031* (2013.01); *G01N 30/722* (2013.01); *G01N 33/0027* (2013.01); *H01J 49/24* (2013.01); *G01N 2030/025* (2013.01); *H01J 49/0022* (2013.01)

(58) Field of Classification Search
CPC .... H01J 49/0031; H01J 49/24; H01J 49/0022; H01J 49/0427; G01N 30/722; G01N 33/0027; G01N 2030/025; G01N 33/0011
USPC ......................................... 250/281, 282, 288
See application file for complete search history.

(56) References Cited

U.S. PATENT DOCUMENTS

| | | | |
|---|---|---|---|
| 4,433,982 | A | 2/1984 | Odernheimer et al. |
| 8,648,293 | B2 * | 2/2014 | Correale ............... G01N 1/2202 250/252.1 |
| 8,809,773 | B2 | 8/2014 | Bier |
| 8,822,949 | B2 | 9/2014 | Krechmer et al. |
| 10,256,084 | B2 | 4/2019 | Mensa et al. |
| 2011/0011158 | A1 | 1/2011 | Bodily et al. |
| 2014/0283626 | A1 | 9/2014 | McMurtry et al. |
| 2019/0348267 | A1 | 11/2019 | Wright et al. |

* cited by examiner

*Primary Examiner* — Michael Maskell
(74) *Attorney, Agent, or Firm* — Barclay Damon LLP

(57) ABSTRACT

A gas analyzer and a method for performing mass spectrometry analysis includes a membrane configured to receive an input flow of carrier gas. The membrane defines a variable thickness region between first and second positions along an input face of the membrane and separates the analyte sample into an output flow of analyte molecules. A mass spectrometer is disposed downstream of the membrane and includes an input orifice for receiving the output flow. The mass spectrometer is configured to perform a response profile analysis of the analyte molecules in the sample analyte.

24 Claims, 10 Drawing Sheets

GAS ANALYZER AND MEMBRANES THEREFOR

CROSS REFERENCE TO RELATED APPLICATIONS

This application is a non-provisional application filed under relevant portions of 35 U.S.C. 111 and 37 CFR 1.53, and claims the priority and benefit of, U.S. Provisional Patent Application No. 63/008,862, filed on Apr. 13, 2020. The entire contents of such application is hereby incorporated by reference.

TECHNICAL FIELD

This application is directed to the field of membrane mass spectrometry, and more particularly, to an improved membrane inlet for a gas analyzer, such as a chromatograph mass spectrometer.

BACKGROUND

MI/MS (Membrane Interface/Mass Spectrometry) was first described by Hoch and Kok in 1963 and has become a well-known sample introduction technique in the field of mass spectrometry and most importantly in the field of portable mass spectrometry. In portable mass spectrometry, low detection levels are made challenging by the performance limitations inherent to geometrically compact mass spectrometers with limited power and vacuum pumping. MI/MS has been often used to counteract these performance effects, as noted in Voss et al. U.S. Pat. No. 5,426,300.

For instance, a semi-permeable polymer membrane separates the gaseous sample matrix—which is often the effluent of a gas chromatograph (GC)—from the high vacuum region of the mass spectrometer. Analyte molecules pass through the semi-permeable polymer membrane preferentially to the carrier gas because of higher analyte permeability in the membrane relative to the carrier gas permeability in the membrane. Permeability is the product of a molecule's membrane-molecule diffusion coefficient and the molecule's membrane-carrier gas partition coefficient. Semi-permeable polymer membranes are typically silicone-based, however, other polymeric materials have been examined, yielding different advantages and disadvantages. (See Amy J. Maden and, Mark J. Hayward. Sheet Materials for Use as Membranes in Membrane Introduction Mass Spectrometry. Analytical Chemistry 1996, 68 (10), 1805-1811. DOI: 10.1021/ac9509216.). A number of geometries have been explored ranging from planar sheets to column-shaped tubes where the gas flows through or around the tubular membrane, i.e., Cooks et al. U.S. Pat. No. 4,791,292, to systems having multiple membranes, i.e., Wright et al. U.S. Pat. No. 10,755,909. Few of these semi-permeable membranes or columns were suitable for use in a GC/MI/MS.

A limitation to MI/MS in defense and hazardous material (HAZMAT) applications relates to the fact that many low vapor pressure chemicals of concern are larger in size than the environmental targets where MI/MS has historically been most successful. For example, chemical warfare agents like VX, and drugs of abuse like Fentanyl® (is a registered trademark of Janssen Pharmacuticals), these molecules are typically much larger in size than, for example, benzene or tetrachloroethylene. Molecules of larger size typically exhibit very low membrane-analyte diffusion coefficients and as a result these molecules take longer to move through the membrane than smaller molecules. A low membrane-analyte diffusion coefficient degrades the performance or analysis of a GC/MI/MS system inasmuch as the analyte GC peaks are spread or broadened as the molecules diffuse through the semi-permeable membrane. This reduces the resolving power of the GC/MI/MS system as time-resolved peaks exiting the GC overlap, and are smeared together as they enter the MS. The result is reduced detection performance in applications with complex or multi-chemical compounds. It will also be appreciated that such broadened peaks also lower the signal-to-noise ratios compared to peaks which are sharp, i.e., molecules which pass through the membrane quickly so as to rise and fall sharply in the GC/MI/MS analysis. According to Fick's Second law of Diffusion, the broadening of a peak is proportional to the square of the membrane's thickness, so that a thin membrane better preserves chromatographic performance. On the other hand, it can be challenging to make a membrane extremely thin inasmuch as the membrane must support a pressure differential of at least atmospheric pressure on the GC side while maintaining a low vacuum pressure on the MS side. That is, the pressure differential can rupture a very thin membrane, particularly if the membrane is heated to speed diffusion, or reduce other sticking-time constants of a molecule as it passes through the interface. A solution to this problem is taught in Wolcott, et al. U.S. Pat. No. 8,956,696, wherein a method is described for fabricating an ultrathin MI/MS membrane. Therein, large molecule analysis becomes more accessible in a GC/MI/MS analysis. However, a limitation to the method described in the Wolcott et al. '696 patent relates to the increased amount of carrier gas flowing into the GC/MI/MS system. Small pumps and consumable getter pumps can only tolerate limited gas loads. To counteract the vulnerabilities of thin or ultrathin membranes, the area of the membrane must be correspondingly small. This is due to the relationship between the gas loads and the membrane thickness, i.e., the steady-state gas load is inversely proportional to the membrane thickness and directly proportional to the membrane area as described by Fick's First law of Diffusion For low vapor pressure chemicals, a small membrane area is generally ideal because high partition coefficient analytes are rapidly depleted from the vapor stream as they exit the GC column. A larger area of membrane provides no advantage for low volatility chemicals because the low vapor pressure analyte is depleted from the column effluent stream within a short distance where the vapor stream first makes contact with the membrane. A larger membrane area allows more carrier gas to flow into the mass spectrometer without the additional benefit of more analyte. Excess carrier gas is also undesirable because it must be pumped away to maintain acceptable vacuum levels, i.e., requiring larger pumps or more rapid consumption of getter pumps. Excess carrier gas can also degrade the performance of the mass spectrometer because of an increased space charge and increased ion-neutral collisions.

A limitation with respect to the current state-of-the-art GC/MI/MS systems relates to the same ultrathin interface which is not well-suited for high vapor pressure analyte applications (e.g., HCN or Sarin). This is due to the fact that: (i) high vapor pressure chemicals have a propensity for lower membrane-air partition coefficients and (ii) these chemicals require more membrane contact before fully depleting the vapor stream. However, since these chemicals are typically smaller, they tend to have higher polymer-analyte diffusion coefficients. This means that a thicker membrane is tolerable inasmuch as the broadening of GC peaks will not be significant i.e., the GC peak-shape will not degrade. Accordingly, in those cases where optimization is required for volatile chemicals, a thicker membrane is advantageous because it reduces the amount of carrier gas flowing into the mass spectrometer over the required membrane area to fully extract the sample analyte from the carrier.

U.S. Pat. No. 8,648,293 teaches the use of a MI/MS for calibration of an MS system wherein a substantially planar membrane is constructed from silicon (Si), and/or silicon nitride (SiN) with a thick region and a thin region in the center. A system of this type does not benefit from enhancement of analyte transport afforded by differential permeation rates of analyte and carrier through a semipermeable membrane. Additionally, no use can be made of the thicker region to also permit higher vapor pressure gases into the MS because this region is gas-tight.

U.S. Pat. No. 10,755,909 teaches of a MI/MS system using of multiple membranes having different thicknesses to enhance the sensitivity and time response to distinguish between different chemicals. A disadvantage of this system relates to the fact that intervening components/volumes degrade the GC peak shape or otherwise interact unfavorably with chemicals prone to degradation. Another disadvantage is that for optimization of many chemicals having differing permeation behavior, many separate membranes are needed but are not compatible with chromatographic separation. For example, with 2 membranes, only one low vapor pressure and one high vapor pressure chemical can be simultaneously optimized. A method to optimize for a wide range of chemicals are still necessary to deliver sharp GC peaks.

A need, therefore, exists for a semipermeable membrane useful for analyzing chemicals having a wide spectrum of vapor pressure characteristics but which is suitably thin and/or small so as to be compatible with the low carrier gas flow rates used in modern gas chromatography.

SUMMARY OF THE DISCLOSURE

In one embodiment, a gas analyzer is provided for analyzing a sample having one or more analytes flowing in a carrier gas. The gas analyzer includes a membrane configured to receive an input flow of carrier gas. The membrane defines a variable thickness region between first and second positions along an input face of the membrane and functions to produce a concentrated or enriched flow of analyte molecules. That is, the membrane rejects most of the carrier gas and allows a highly concentrated flow of analytes molecules through the membrane. The membrane is supported by a housing defining an aperture for directing an output flow of analyte molecules into a mass spectrometer which is disposed downstream of the membrane. The mass spectrometer performs and analysis of the analyte molecules to identify the chemical elements of the analyte sample.

In another embodiment, the gas analyzer includes a housing for receiving the membrane, which housing includes an output nozzle directing the analyte sample over the input face of the membrane. The output nozzle generally complements the geometric shape of the input face to evenly distribute the analyte sample thought the membrane. That is, the output nozzle of the housing in combination with the input face of the membrane channels carrier gas across the variable thickness region from the first to the second positions.

In another embodiment, a method is provided for membrane mass spectroscopy analysis of an analyte sample comprising the steps of: directing the sample analyte to an input face of a membrane defining first and second positions, which membrane defines a variable thickness region between the first and second positions along an input face of the membrane. The variable thickness region of the membrane is functionally operative to concentrate an output flow of analytes for analysis by a mass spectrometer. The mass spectrometer produces a response profile for identifying the analytes of the analyte sample.

In another embodiment, a membrane is provided for a gas analyzer which membrane is disposed between an output nozzle and a support surface of a housing. The membrane comprises a variable thickness region between a first position and a second position, wherein the variable thickness region defines a first thickness dimension at the first position and a second thickness dimension at the second position. The first thickness dimension is less than the second thickness dimension so as to produce a concentrated output flow of analytes in the analyte sample.

The above embodiments are exemplary only. Other embodiments as contemplated and fall within the scope of the disclosed subject matter and appended claims.

BRIEF DESCRIPTION OF THE DRAWINGS

So that the manner in which the features of the disclosure can be understood, a detailed description may be had by reference to certain embodiments, some of which are illustrated in the accompanying drawings. It is to be noted, however, that the drawings illustrate only certain embodiments and are therefore not to be considered limiting of its scope, for the scope of the disclosed subject matter encompasses other embodiments as well. The drawings are not necessarily to scale, emphasis generally being placed upon illustrating the features of certain embodiments. In the drawings, like numerals are used to indicate like parts throughout the various views, in which.

Corresponding reference characters indicate corresponding parts throughout several views. The examples set out herein illustrate several embodiments, but should not be construed as limiting in scope in any manner.

DETAILED DESCRIPTION

The present disclosure relates to gas analyzers and membranes used in gas analyzers. Specifically, different membrane geometries are presented that represent a marked improvement over conventional membranes when used in membrane interface mass spectroscopy (MI/MS).

Advantageously, various embodiments demonstrate how to geometrically optimize a GC/MI/MS interface for the detection of chemicals spanning a range of vapor pressures while minimizing the carrier gas load into the instrument. The gas analyzer is characterized by a compact design envelope which is compatible with fast chromatography.

Advantageously, the present disclosure provides a portable GC/MI/MS system that permits large, medium, and small analyte molecules into the mass spectrometer while minimizing the flow of carrier gas and preserving the shape of the signal amplitude vs. time domain output plot. By providing a single membrane with a variable thickness, the membranes described herein can be geometrically optimized for a wide range of vapor pressures while minimizing carrier flow into the mass spectrometer. By contrast, and as mentioned in the Background section of this disclosure, conventional systems include membranes with a single thickness, such as thin membranes or thick membranes, configured as tubes or flat membranes.

As explained in further detail below, the present disclosure provides a GC/MI/MS interface with a stepped or graded membrane, achieved either through variable thickness, temperature gradients, materials selection, or a combination thereof. In one embodiment, the GC/MI/MS interface is configured such that column effluent is directed at the thinnest portion of a variable thickness membrane with the gas then flowing substantially in the direction of a gradient of increasing membrane thickness, for example laterally across an input face of the membrane. The membrane may be axially symmetric or horizontally asymmetric, i.e., in a plane defined by the membrane. In one example, the membrane is supported by a single support. In yet another example, the membrane is in a single housing. In still another embodiment, the GC/MI/MS interface is configured such that the effluent is directed from the column onto the thinnest portion of a semi-permeable membrane having two (2) or more layers so that the gas passes substantially over a thin region prior to passing over a thicker region. In a further embodiment, the GC/MI/MS interface is configured such that the effluent is directed from the column onto a region of a semi-permeable membrane so that the gas passes substantially over a portion with the highest analyte permeability prior to passing over a region containing polymers of lower analyte permeability. In any of the above examples, rather than GC, a gas analyzer may use air as a carrier gas and the air is directed over the membrane interface with a pump, e.g., applicable to other sources of the sample analyte.

Figure 1:
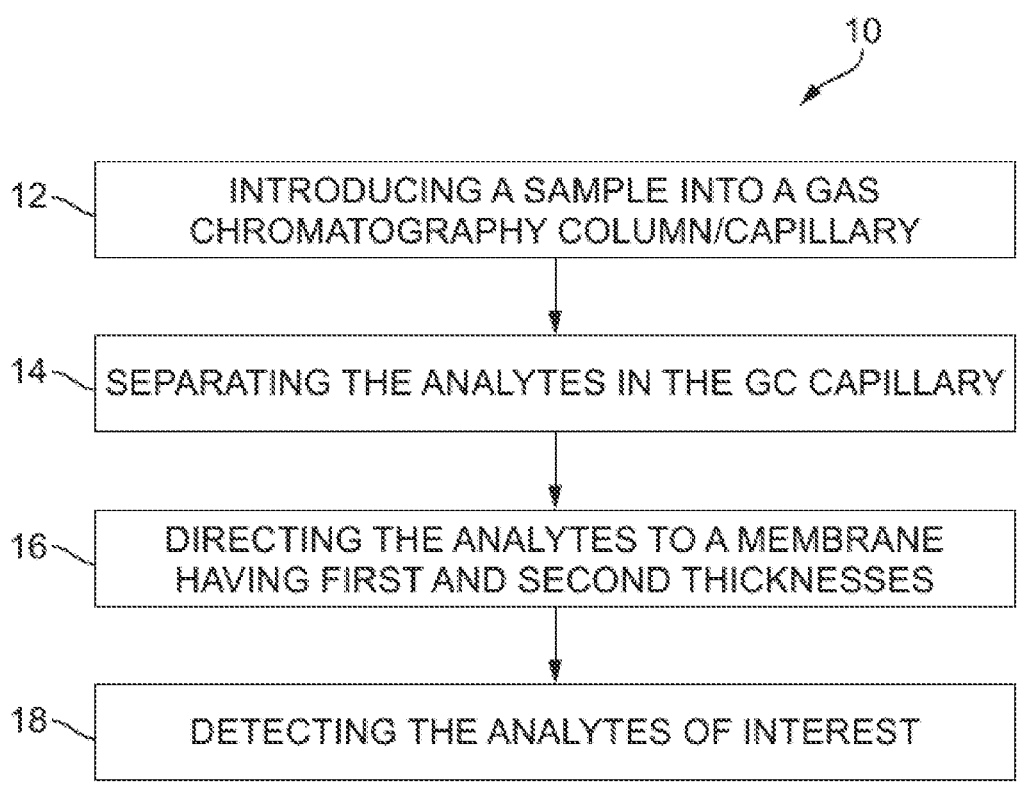
FIG. 1 is a flowchart of a method for analyzing a sample, in accordance with one or more aspects set forth herein.

By way of general overview, FIG. 1 is a flowchart of a method 10 for analyzing a sample analyte. In the embodiment of FIG. 1, the method 10 at block 12 begins by introducing an analyte sample into a GC column or capillary. The analyte sample includes various analytes flowing in a carrier gas. Next, at block 14, the analytes in the analyte sample separate within the GC column.

Next, at block 16, the analytes are directed to a membrane, which may be a semi-permeable membrane as noted above. The membrane separates the analytes from the carrier gas. In one example, the membrane has a first thickness at a first position and a second thickness at a second position. In such a case, a first analyte interacts with the membrane at the first position and a second analyte interacts with the membrane at the first and second positions. In another example, a molecular mass of the first analyte is greater than a molecular mass of the second analyte and the second thickness is greater than the first thickness. In a further example, the first analyte has a first diffusion coefficient and the second analyte has a second diffusion coefficient, and a distance between the first and second positions is selected to facilitate the second analyte interacting with the membrane at the second position. In one or more embodiments, an average time for the first analyte to traverse the membrane at the first position is similar to the average time for the second analyte to traverse the membrane at the second position. For instance, the first and second thicknesses and the first and second positions are selected to prevent undue broadening or lateral spread of the mass spectroscopy peaks associated with the first and second analytes.

In one specific example of membrane may have a (i) concave curvilinear, (ii) linearly-tapered or (iii) plano-concave geometric contour from the first to the second positions along the variable thickness region. These geometric contours facilitate the passage of larger molecules to pass through at the first position and smaller molecules to pass through both the first and second positions along the input face of the membrane. Finally, after passing through the membrane, the analytes of interest may be detected, at block 18, by a mass spectrometer.

Figure 2:
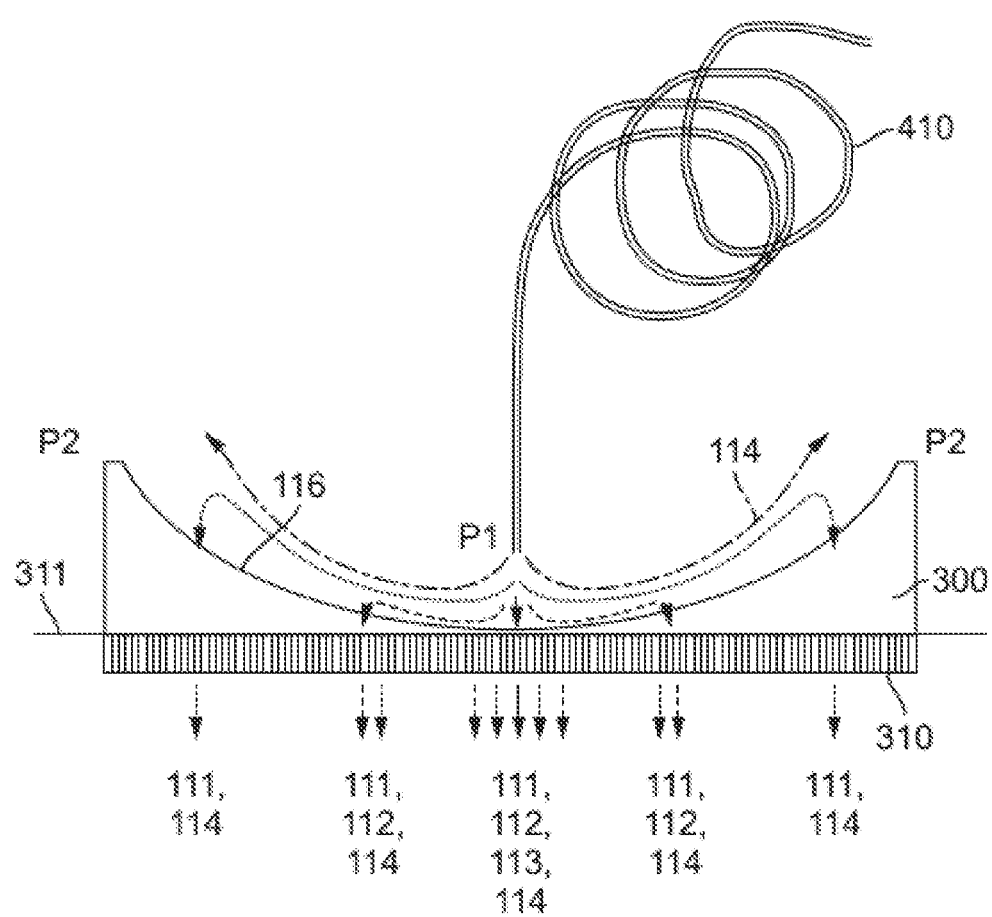
FIGS. 2 and 2A depict gas analyzers having a membrane disposed therein for separating an analyte sample into its constituent, analyte molecules, in accordance with one or more aspects set forth herein.
Figure 2A:
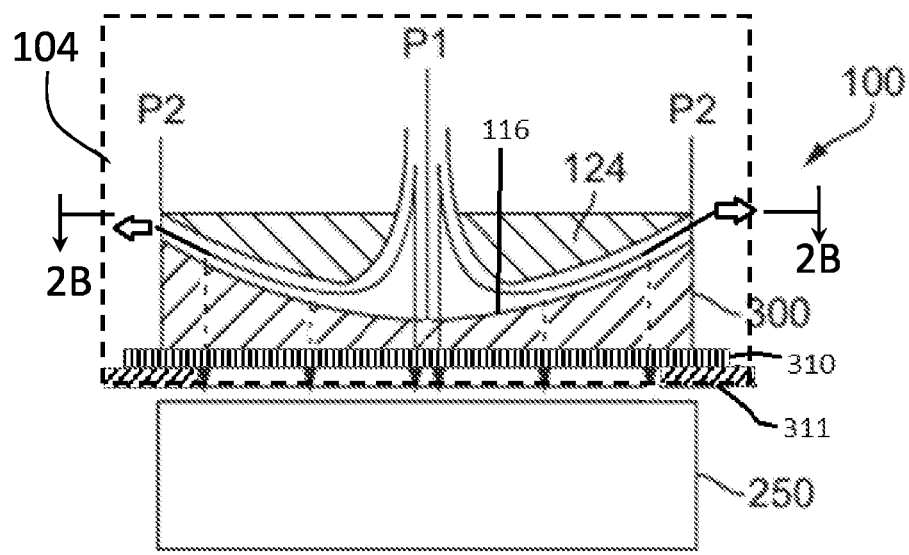
Figure 4A:
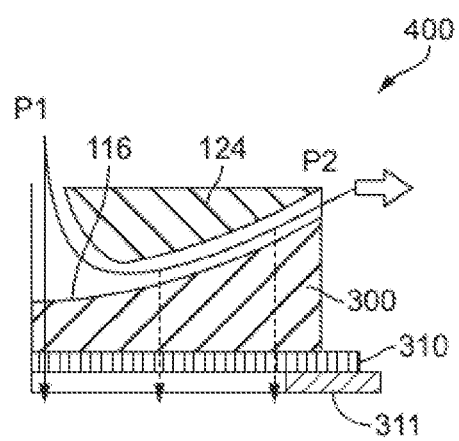
FIGS. 3, 4 and 4A depict alternate embodiments of the gas analyzer and membranes useful therein.
Figure 2B:
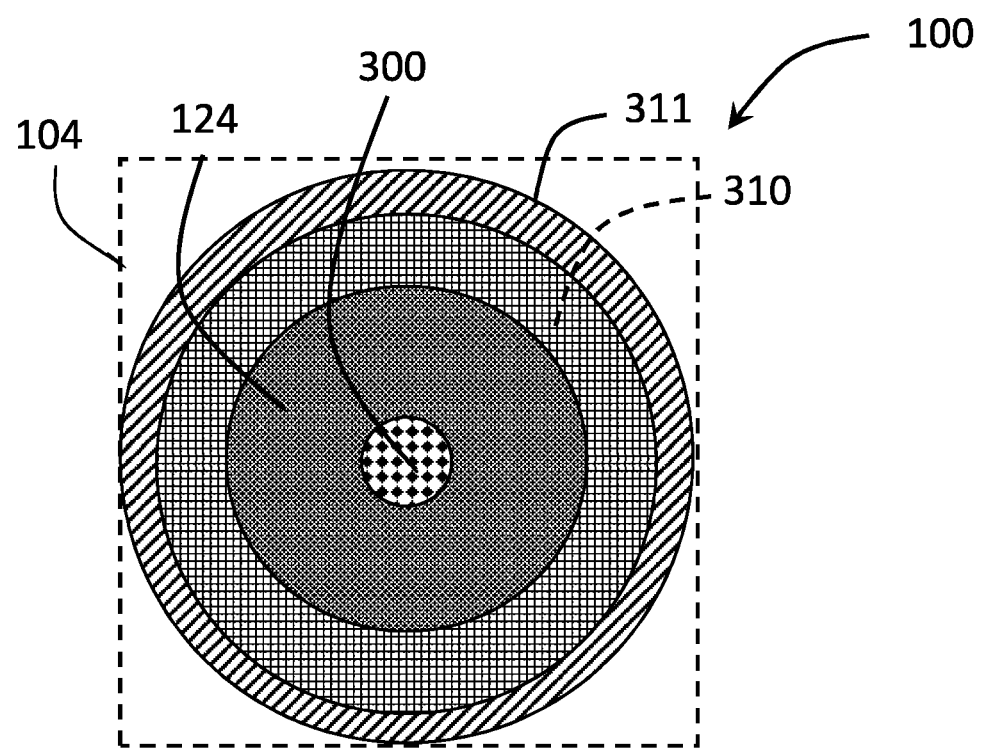
FIG. 2B is a top view of the gas analyzer shown in FIG. 2A taken along line 2B-2B of FIG. 2A.

FIGS. 2, 2A and 2B depict a gas analyzer 100 including a membrane 300 disposed within a housing 104 operative to direct a flow of carrier gas 114 along the input face 116 of the gas analyzer 100. The membrane 300 is positioned on a support 310, 311 comprising a porous center 310 supported by a non-porous outer ring 311 which defines an aperture for receiving an output flow of analyte molecules 111, 112 and 113 from the membrane 300. The carrier gas 114 is largely rejected and exhausted radially outboard to each side of the membrane (i.e., in the direction of the right and left arrows shown in FIG. 2A. The membrane produces a concentrated flow analyte molecules through the aperture in the support structure 310, 311. The analyte molecules 111-113 are directed downstream to a mass spectrometer 250 for detection.

The geometry of membrane 300 includes a variable thickness region VR from a first position P1 to a second position P2. That is, the membrane 300 is selected such that it is thin at the first position P1 where the gas chromatography (GC) effluent vapor stream contacts the membrane 300, i.e., upon deposition or output from a GC capillary tube or column 410. Low volatility molecules 113 are depleted from the carrier gas near this initial point of contact due to typically high membrane-air partition coefficients. These are the molecules which require a very thin membrane for producing a fast response (molecules similar to Fentanyl). The variable thickness region VR of the membrane 300, is positioned on the porous support 310, and becomes gradually or incrementally thicker as the distance increase from the first position P1 to the second position P2. This facilitates an increase in the total membrane area and allows the passage of smaller molecules 112 having a more moderate vapor pressure such as Sarin molecules 112. Sarin typically has higher membrane diffusion coefficients and can tolerate a thicker membrane region. Molecules 111 such as HCN or some other very volatile vapor, or gas have a low partition coefficient so more area is needed before depleting the vapor stream.

The housing 104 may include a column or conduit 124 configured to distribute the carrier gas 114 uniformly over the input face or face surface 116 of the membrane 300. In one embodiment, the housing 104 includes an output column or nozzle 124 which complements the geometric shape of the face surface 116 to evenly distribute the input flow of carrier gas 114 over the face surface 116 of the membrane 300. In this embodiment, an output face of the membrane 300 engages a porous support surface 310 such that the analytes may flow through an aperture of the support surface 310 and into the mass spectrometer 250.

In one method, the membrane 300 may be fabricated by silicone imprint molding. A high precision mold is prepared by grinding operations typically used for the production of high precision optical lenses such as those made from BK7 glass. The mold is laid flat and a thin stainless steel ring is clamped around the perimeter of a glass mold to create a form. A silicone mold release such as Dow Corning—Molykote 316 is applied to the assembly and a polymeric mixture of Dow Corning Sylgard 184 is used to make the membrane itself. A base and an activator are mixed in the ratio of 10:1 before pouring the forms. The membrane 300 may be air dried and baked at 100 C for 1 hr. to complete the cure. Other post cure operations such as rinsing with toluene may also be used to remove uncured base or mold release agents.

Figure 3:
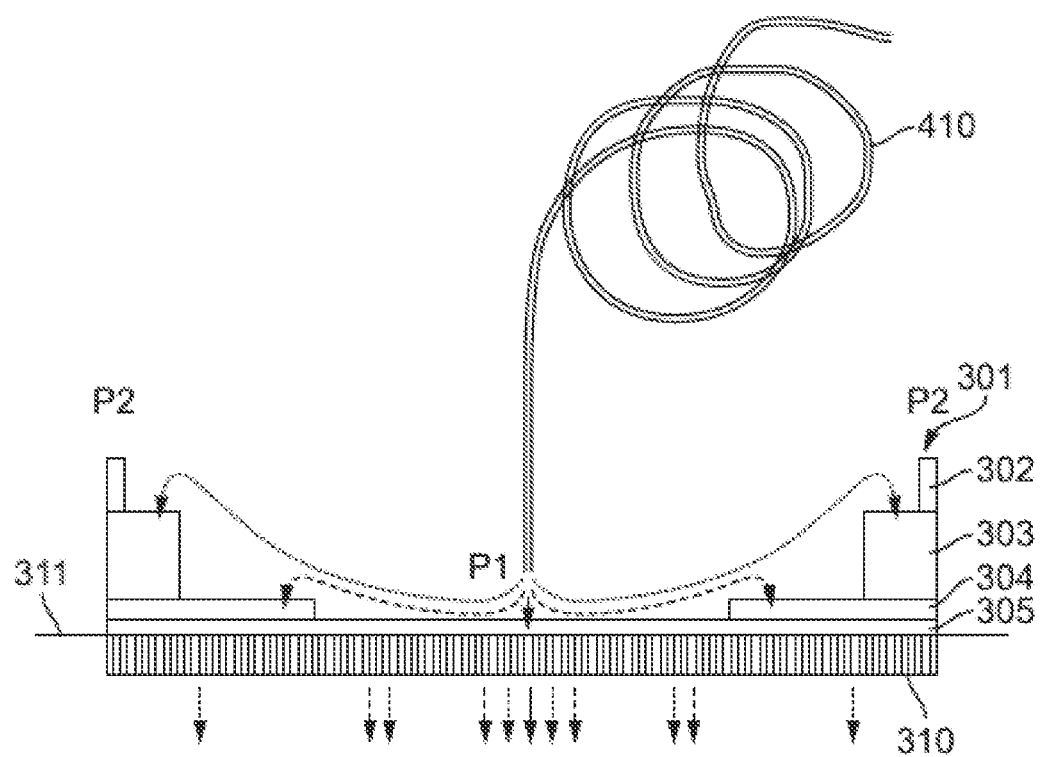
Figure 4:
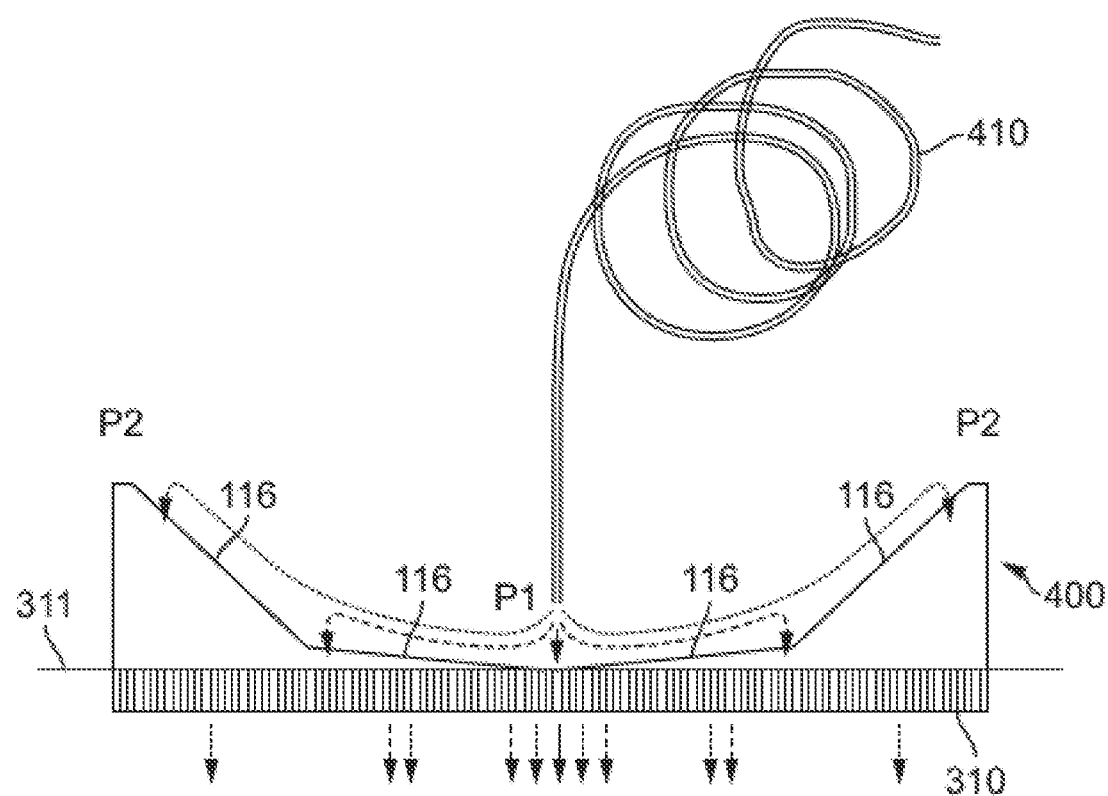

In FIG. 3, another method of fabrication includes an ultrathin membrane, i.e., 1-4 microns thick, may be prepared directly on a support such as that disclosed in U.S. Pat. No. 8,956,696, the contents being incorporated herein in their entirety. In a second step, thin rings of silicone sheet such as those commercially available from Wacker silicones (in a thickness of about 25 microns), are cut out in rings of different size. This may be done using convention techniques such as by die cutting. These rings may be aligned on a central axis to create a stepped structure. A single type of silicone can be employed or different semipermeable, typically polymeric, materials can be used for each step. Although this technique has certain advantages in ease of construction, stepped edges create local turbulence in the gas flow. The steps tend to be large relative to the thinnest layer. The inner diameter of the smallest ring may be about 2 mm. This must be only slightly larger than the inner diameter of a GC capillary column which is typically about 0.18, 0.25, or 0.32 mm. The entire membrane may have a diameter of about 10 mm diameter and as little as about 5.0 mm. Small dimensions are necessary as the column flow can be less than 1 ml/min and GC peaks can be less than 1 second. Larger areas can smear or distort peaks shapes.

In the described embodiment, a filament produces electrons to ionize the carrier gas and analytes. The resulting ions are extracted from the ionization region with lenses for mass analysis. The mass spectrometer detector can be any of a variety of types including a magnetic sector, a time of flight (TOF), a quadrupole filter, or an ion trap.

In this design, the membrane 300 is truncated at the point 311 by an impermeable region of the support material below the membrane. No analyte or carrier gas can flow through this impermeable region of the support. The radial dimension to stop flow into the MS (where 310 stops and 311 starts) is chosen because at the point where the ratio of target analyte to carrier gas 114 falls below a desired threshold. The position of 311 can be moved inward as a design decision. This, for example, could occur at half the radius depicted in FIG. 2. This would tune the interface by increasing the ratio of low to high vapor pressure analyte and similarly the ratio of low vapor pressure analyte to carrier gas.

The membrane 300 depicted in FIG. 3 comprises discrete membrane layers 302, 303, 304, 305. These membrane layers 302, 303, 304, 305 can be the same material (e.g., the semi-permeable membrane materials noted above), but it is known to use different membrane materials for selectivity properties. This design affords a method to select different membrane properties to tune the permeation properties and mechanical stability required for different chemicals. Similar to FIG. 2, the membrane thicknesses are optimized so that low volatility, higher membrane air partition coefficient molecules may traverse the thin center region, and the higher volatility, lower membrane air partition coefficient molecules may traverse the thinner regions and also the thicker outer regions.

Note that the FIG. 3 membrane embodiment is made of discrete layers that come together to approximate the shape as the FIG. 2 membrane embodiment. All of the membrane geometries that are described herein as a smooth shape may also be made in a similar layered manner for ease of manufacturing. Applicant has determined that a layered shape that approximates, or is substantially the same as, a smooth shape can have nearly the same properties of the smooth shape, and may be used where manufacturing simplicity is desired. While the layered shape will produce a similar concentration of analytes, the stepped face surface may produce more turbulence in the flow of carrier gas. As such, peak shapes of the response profile may be broader when employing a stepped membrane geometry.

FIG. 4 depicts a membrane 300 that has the same general shape as membrane of FIG. 2, but has a tapered linear input face surfaces 400. Again, the membrane 300 has the general shape of being thinner in the center or at a first position P1, and thicker as the position advances outboard toward position P2 proximal to the edge of the membrane 300.

Although the membranes disclosed above in FIGS. 1-4 demonstrate radial symmetry, they could also have different geometries. For example, the membranes may only be a half-circle shape or may have an inner concavity shaped like a pipe or half pipe such as the membrane 300 shown in FIG. 4A. In such cases, the output nozzle 124 of the GC capillary 410 would be positioned such that the gas and vapors exiting the capillary first encounter the thin region of the membrane.

In another embodiment, the shape of the curve showing membrane thickness in FIG. 2 can be tuned to account for the importance of volatile chemicals relative to low volatility chemicals. A flatter thin area in the center, proximal to P1, will improve low volatility chemicals. But since we typically want to keep the amount of carrier gas entering the MS low, the membrane thickness could then be increased more quickly in the than depicted in FIG. 2. Accordingly, the curvilinear contour may resemble an asymptotic or parabolic shape.

With respect to the membrane support 310, this can be constructed using meshes or frits. But in cases where the membrane is self-supporting, the area of this aperture can be defined by a mechanical shutter similar to a camera iris to dynamically adjust the range of chemicals entering the mass spectrometer. In another example, concentric regions of the support can be provided that are blocked like shown in reference number 311 and then open again as you move further out. This can advantageously help tune for low- and high-volatility, without the need for mid-volatility.

In yet another embodiment, a temperature gradient rather than a change of thickness may be used to create the desired behavior since the membrane air partition coefficients and membrane analyte diffusion coefficients both vary with temperature. Generally the membrane air partition coefficient will decrease with increasing temperature while the polymer analyte diffusion coefficient will increase with increasing temperature. This means that a hot region positioned at the column exit will favor low volatility (and typically larger) analyte by providing fast diffusion coefficients. A cooler region further out will benefit higher volatility analyte by increasing their membrane air partition coefficients relative to the hotter region in the center of the device. The cooler region also reduces the carrier gas flow into the MS. In a similar manner, rather than using varying thickness to achieve the gradient in partitioning behavior, a polymer blend with appropriate material properties that vary along the membrane may be used.

Figure 5A:
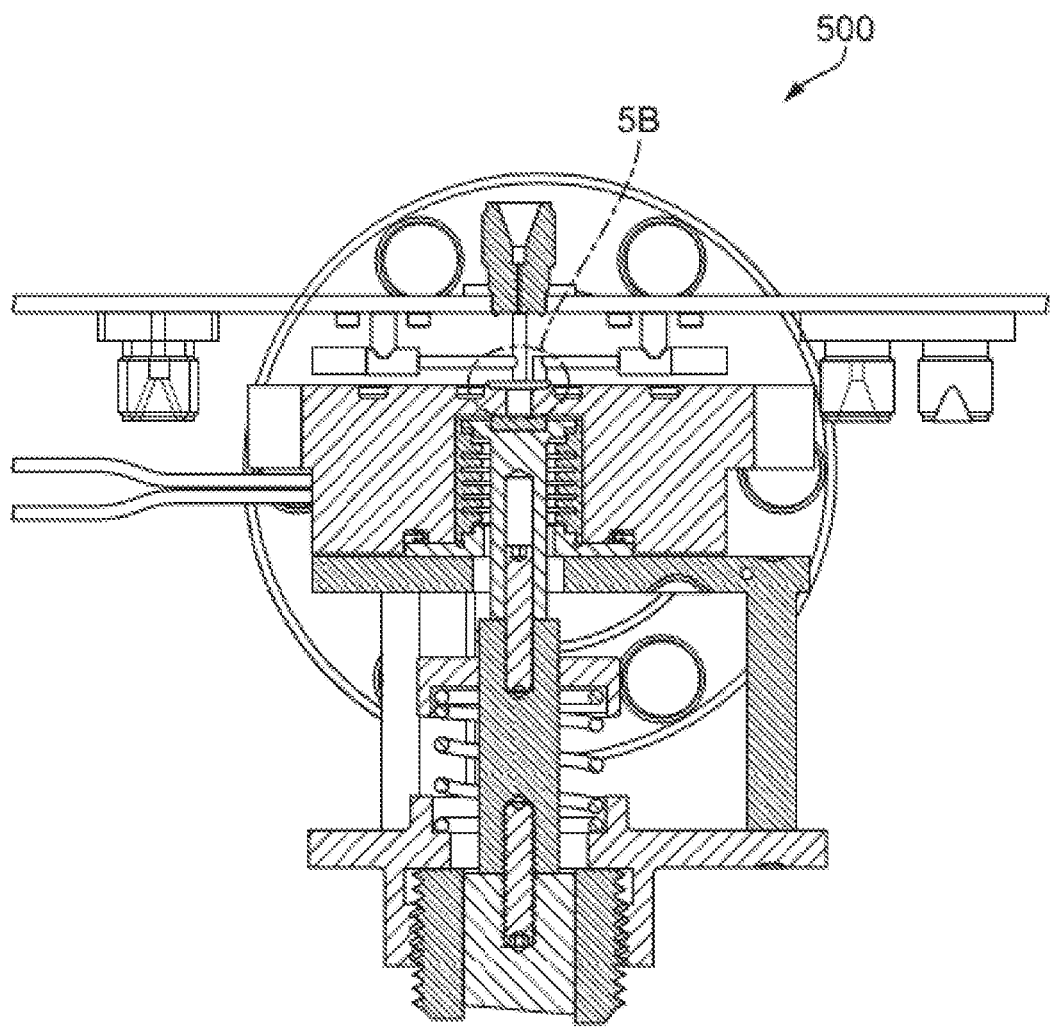
FIGS. 5A-5C depict a housing that creates a flow path for isolating the input flow of carrier gas from an output flow of analyte molecules upon being concentrated by the membrane in accordance with another embodiment of the disclosure.
Figure 5B:
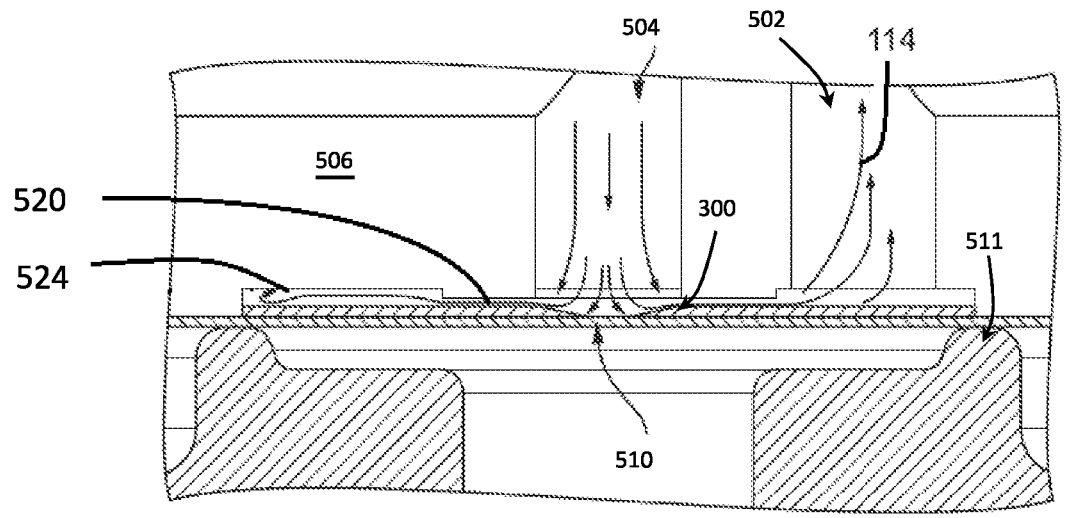
Figure 5C:
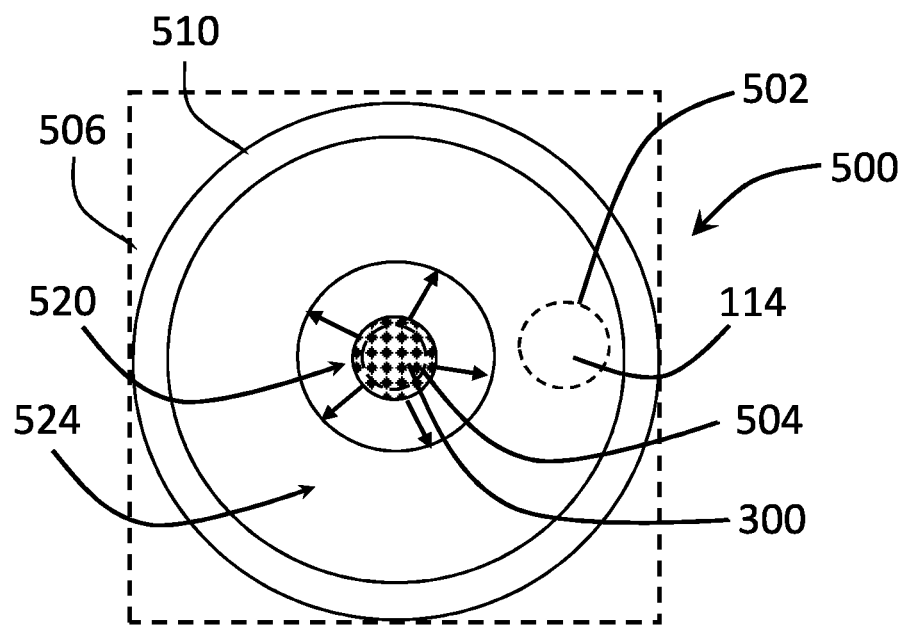

In FIGS. 5A-5C, a membrane 300 is provided for use in a gas analyzer 500. which exhausts carrier gas 114 laterally or radially to an exhaust conduit 502. More specifically, an input flow of carrier gas 114, i.e., containing an analyte sample, is pumped or injected into an input nozzle 504 of a housing 506. The membrane is received within the housing 506 and is supported by a structure 510 having a porous region disposed within and along a circular support 511. The circular support structure 511 defines an aperture for receiving the analyte molecules which are passed by the membrane 300 and identified by a mass spectrometer 250 disposed downstream of the porous support 510.

In the described embodiment, the housing 506 defines a lateral or circular channel 520 which is in fluid communication with the input nozzle 504 at one end and a ring-shaped plenum 524 at the other end. Moreover, the ring-shaped plenum 524 is in fluid communication with the exhaust conduit 502 of the housing 506 for exhausting carrier air 114 away from the mass spectrometer 250. As shown in FIG. 5B, the input nozzle 504 from a GC column sends carrier gas and analytes downward towards the membrane 300, which may be any of the membranes discussed above. In such a case, axial symmetry of the gas flow is achieved. This housing 506 establishes the gas channel 520 which causes flow from the center of the membrane 300 to a radially outboard position proximal to an edge of the membrane 300. In one embodiment the thickness of the fluid channel is substantially smaller than the distance between the first and second positions to ensure that gas mixing is minimized and that gas does not flow or diffuse radially inboard from an edge to the center of the membrane 300. In another embodiment the channel dimensions are such that the flow is largely laminar. In a preferred embodiment, the membrane is thinnest in the entire region across from the gas inlet feature or tube. In another embodiment, a linear channel may be located across the membrane 300.

Figure 6:
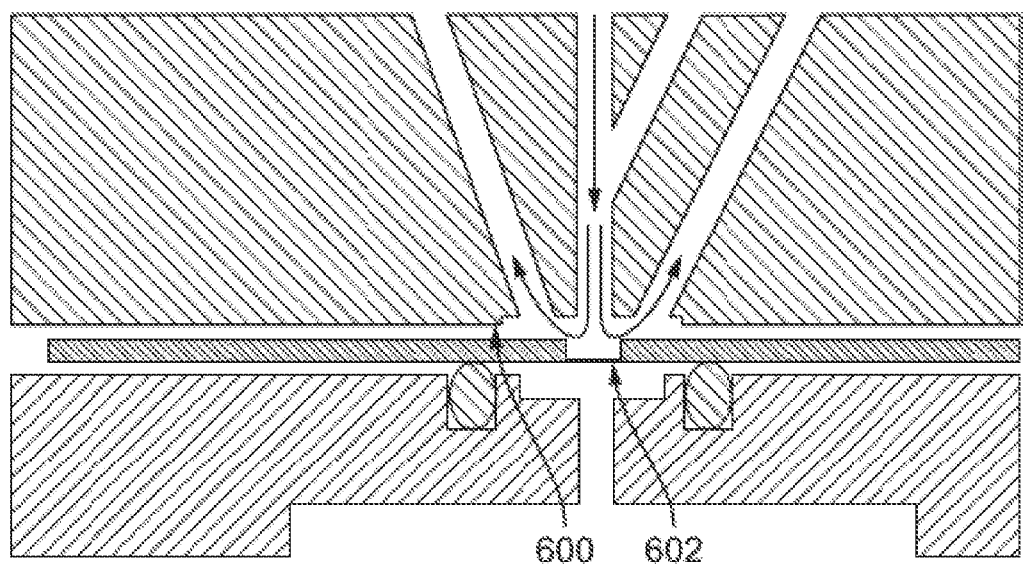
FIG. 6 depicts another membrane for use in a gas analyzer, in accordance with one or more aspects set forth herein.

FIG. 6 depicts another membrane 600 for use in a gas analyzer. In this embodiment, the membrane 600 has an ultrathin portion 602 which is selected to facilitate analysis of specific low volatility molecules. A thicker region facilitates the detection of volatile chemicals while minimizing the carrier gas from entering the system.

Figure 7:
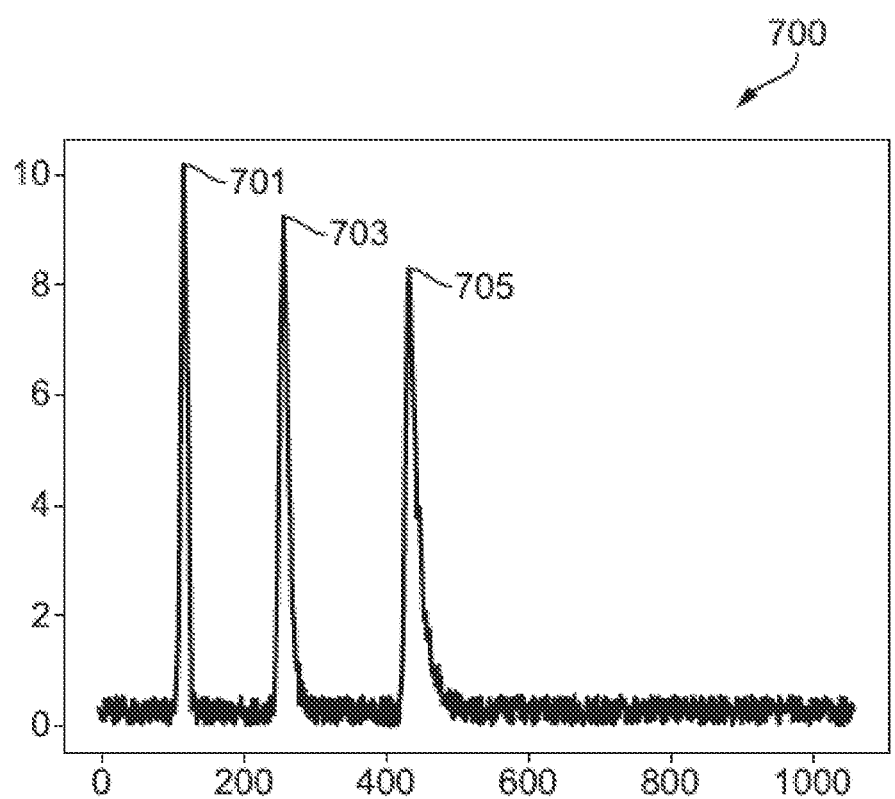
FIG. 7 depicts simulated GC/MI/MS response profiles for three (3) chemicals separated by the membrane and identified by the GC mass spectrometer.

FIG. 7 depicts simulated GC/MI/MS response chromatograms (e.g., the total ion chromatograms for chemicals eluting from the GC) for 3 chemicals. The vertical axis is signal amplitude. The horizontal axis is time in seconds. The response to three chemicals is shown. The response to a small molecule eluting from the GC and being detected by the MS is shown at 701. A small molecule typically has a high vapor pressure, a low membrane carrier partition coefficient, and a high polymer analyte diffusion coefficients. Low membrane carrier partition coefficients are typically well correlated to low column phase carrier partition coefficients because membrane materials and GC column phase are often very similar materials. The result is that these chemicals typically elute from the GC early. A large molecule elutes at 705. Larger molecules typically have low vapor pressures, high membrane carrier partition coefficients, and low polymer analytic diffusion coefficients. Large molecules typically elute from the GC later on as these molecules spend more time partitioned into the stationary column phase and less time in the model phase carrier gas. The chemical eluting at 705 is broadened only slightly in its response because of the thin region of membrane where the carrier gas first interacts with the membrane interface disclosed herein. Molecules of intermediate size have intermediate properties and 703 shows a typical intermediate size molecule that elutes in between 701 and 705.

FIG. 7 shows the response profile produced by the gas analyzer 100 of the present disclosure. As will be appreciated from examination of FIG. 7 all three analytes/molecules demonstrate a good signal to noise ratio. FIG. 7 shows the analysis associated with three analytes, but a greater or fewer number of analytes may be analyzed by the gas analyzer. Additional embodiments include any one of the embodiments described above, where one or more of its components, functionalities or structures is interchanged with, replaced by or augmented by one or more of the components, functionalities or structures of a different embodiment described above.

It should be understood that various changes and modifications to the embodiments described herein will be apparent to those skilled in the art. Such changes and modifications can be made without departing from the spirit and scope of the present disclosure and without diminishing its intended advantages. It is therefore intended that such changes and modifications be covered by the appended claims.

Although several embodiments of the disclosure have been disclosed in the foregoing specification, it is understood by those skilled in the art that many modifications and other embodiments of the disclosure will come to mind to which the disclosure pertains, having the benefit of the teaching presented in the foregoing description and associated drawings. It is thus understood that the disclosure is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the present disclosure, nor the claims which follow.

What is claimed is:

1. A gas analyzer for analyzing an analyte sample, comprising:
   a membrane configured to receive an input flow of carrier gas containing the analytes and defining a variable thickness region between first and second positions along an input face of the membrane, the variable thickness region of the membrane being permeable to the analytes and configured to produce a concentrated output flow of analyte molecules;
   a housing including a surface for supporting the membrane and defining an opening configured to receive an output flow of analyte molecules from the membrane; and
   a mass spectrometer receiving the output flow and configured to perform an analysis to detect the analyte molecules in the analyte sample.

2. The gas analyzer of claim 1, wherein a thickness dimension at the first position is less than a thickness dimension at the second position and wherein the variable thickness region incrementally increases from the first to the second positions.

3. The gas analyzer of claim 1, wherein the housing directs the input flow of the carrier gas over the input the of the membrane.

4. The gas analyzer of claim 3, wherein the housing is configured to distribute the carrier gas uniformly over an input face surface of the membrane.

5. The gas analyzer of claim 3, wherein the housing includes an output nozzle which complements a geometric shape of the face surface to evenly distribute the input flow of the carrier gas over an input face surface of the membrane.

6. The gas analyzer of claim 3, wherein the membrane is received within the housing and is disposed between an output nozzle of the housing and the mass spectrometer.

7. The gas analyzer of claim 6, wherein the output nozzle of the housing and the input face of the membrane are configured to direct the input flow of the carrier gas laterally along the variable thickness region of the membrane.

8. The gas analyzer of claim 1, wherein the input face of the membrane defines a concave curvilinear geometric contour from the first to the second positions along the variable thickness region.

9. The gas analyzer of claim 1, wherein the input face of the membrane defines a linearly-tapered geometric contour from the first to the second positions along the variable thickness region.

10. The gas analyzer of claim 1, wherein an output face of the membrane defines a curvilinear geometric contour from the first to the second positions along the variable thickness region.

11. The gas analyzer of claim 1, wherein the membrane defines an intermediate position between the first and second positions, and wherein a first analyte passes through the variable thickness region between the first position and the intermediate position and a second analyte passes through the variable thickness region between the first and second positions.

12. The gas analyzer of claim 11, wherein the first analyte is one of: (i) a higher molecular weight, (ii) a larger molecular size, (iii) a higher membrane carrier gas partition coefficient and (iv) a lower membrane diffusion coefficient, than the second analyte.

13. The gas analyzer of claim 1, wherein the membrane is radially symmetric about the first position.

14. The gas analyzer of claim 1, wherein the variable thickness regions of the membrane comprises a series of vertically stacked and radially stepped layers between the first and second positions.

15. The gas analyzer of claim 1, further comprising a vacuum pump configured to produce a low pressure region downstream of the support of the housing to facilitate passage of the sample analyte through the membrane.

16. A method for membrane inlet, mass spectroscopy analysis of a sample analyte having one or e analytes flowing in a carrier gas, the method comprising the steps of:

directing the sample analyte to an input face of a membrane defining first and second positions, the membrane defining a variable thickness region between the first and second positions along the input the of the membrane, the variable thickness region of the membrane being permeable to the sample analyte and separating the sample analyte into an output flow of analyte molecules; and, directing the output flow of analyte molecules through an aperture of a housing and into a mass spectrometer, and producing an analysis to detect he analyte molecules in the sample analyte by mass spectrometry.

17. The method of claim 16, wherein a thickness dimension at the first position is less than a thickness dimension at the second position and wherein the variable thickness region incrementally increases from the first to the second positions.

18. The method of claim 17, wherein molecular weight of a first analyte is greater than the molecular weight of a second analyte, and wherein a second thickness is greater than the first thickness.

19. The method of claim 18, wherein the first analyte has a first diffusion coefficient and the second analyte has a second diffusion coefficient, and a distance between the first and second positions is selected to facilitate the second analyte interacting with the membrane at the second position.

20. The method of claim 19, wherein the membrane is radially symmetric about the first position.

21. A membrane for a gas analyzer for analyzing an analyte sample comprising one or more analytes flowing in a carrier gas, the membrane configured for positioning between an output nozzle and a support surface of the gas analyzer, the output nozzle depositing the analyte sample at a first position of the membrane, the membrane comprising a variable thickness region between the first position and a second position, the variable thickness region defining a first thickness dimension at the first position and a second thickness dimension at the second position, wherein the first thickness dimension is less than the second thickness dimension, and wherein the variable thickness region is permeable to the one or more analytes in the analyte sample.

22. The gas analyzer of claim 21, wherein the variable thickness region incrementally increases from the first to the second positions.

23. The gas analyzer of claim 21, wherein an input face of the membrane defines a concave curvilinear geometric contour from the first to the second positions along the variable thickness region.

24. The gas analyzer of claim 21, wherein an input face of the membrane defines a linearly-tapered geometric contour from the first to the second positions along the variable thickness region.

* * * * *

UNITED STATES PATENT AND TRADEMARK OFFICE
CERTIFICATE OF CORRECTION

PATENT NO. : 11,569,079 B2
APPLICATION NO. : 17/229414
DATED : January 31, 2023
INVENTOR(S) : Shawn M. Briglin It is certified that error appears in the above-identified patent and that said Letters Patent is hereby corrected as shown below:

In the Claims

Claim 16
Column 11
Line 54 change "one or e" to --one or more--

Claim 16
Column 12
Line 4 change "input the of the" to --input of the--

Claim 16
Column 12
Line 12 change "detect he" to --detect the--

Signed and Sealed this
Fourteenth Day of March, 2023

*Katherine Kelly Vidal*
Katherine Kelly Vidal
*Director of the United States Patent and Trademark Office*